(12) United States Patent
Lee et al.

(10) Patent No.: US 8,895,727 B2
(45) Date of Patent: Nov. 25, 2014

(54) METHOD FOR PREPARATION OF FLUORINE-18-LABELED FLUMAZENIL USING DIARYLIODONIUM SALT PRECURSOR

(71) Applicant: Bio Imaging Korea Co., Ltd., Seoul (KR)

(72) Inventors: Byung Chul Lee, Seoul (KR); Byung Seok Moon, Gyeonggi-Do (KR); Ji Sun Kim, Gyeonggi-do (KR)

(73) Assignee: Bio Imaging Korea Co., Ltd., Seoul (KR)

( * ) Notice: Subject to any disclaimer, the term of this patent is extended or adjusted under 35 U.S.C. 154(b) by 0 days.

(21) Appl. No.: 14/087,537

(22) Filed: Nov. 22, 2013

(65) Prior Publication Data

US 2014/0081018 A1     Mar. 20, 2014

Related U.S. Application Data

(63) Continuation of application No. PCT/KR2011/004075, filed on Jun. 3, 2011.

(30) Foreign Application Priority Data

May 25, 2011    (KR) .................. 10-2011-0049726

(51) Int. Cl.
*C07D 487/04*     (2006.01)
*A61K 31/5517*    (2006.01)
(52) U.S. Cl.
CPC .......... *C07D 487/04* (2013.01); *A61K 31/5517* (2013.01)
USPC ....................................... 540/496
(58) Field of Classification Search
USPC ........................................ 540/496
See application file for complete search history.

(56) References Cited

U.S. PATENT DOCUMENTS

2009/0069592 A1     3/2009    Suzuki et al.

OTHER PUBLICATIONS

Cai, Lisheng et al., "Chemistry with [18F]Flouride Ion", Eur. J. Org. Chem., 2008, 2853-2873.
Mandap, Katheryn et al., "Development of microwave-based automated nucleophilic [18F] flourination system and its application to the production of [18F]flumazenil", Nuclear Medicine and Biology, 36 (2009) 403-409.
Massaweh, Gassan et al., "Improved work-up procedure for the production of [18F]flumazenil and first results of its use with a high-resolution research tomograph in human stroke", Nuclear Medicine and Biology, 36 (2009) 721-727.
Moon, Byung Seok et al., "Facile aromatic radiofluorination of [18F]flumazenil from diaryliodonium salts with evaluation of their stability and selectivity", Org. Biomol. Chem., 2011, 9, 8346-8355.
Odano, Ikuo et al., "[18F]Flumazenil binding to central benzodiazepine receptor studies by PET—Quantitative analysis and comparisons with [11C]flumazenil-", NeuroImage 45 (2009) 891-902.
Ryzhikov, Nikolaj N. et al., "Preparation of highly specific radioactivity [18F]flumazenil and its evaluation in cynomolgus mokey by positron emission tomography", Nuclear Medicine and Biology, 32 (2005) 109-116.

*Primary Examiner* — Bruck Kifle
(74) *Attorney, Agent, or Firm* — Edwards Wildman Palmer LLP; Kongsik Kim (57) ABSTRACT

Disclosed is the synthesis of [$^{18}$F]flumazenil that is useful in imaging epileptic lesions by PET (positron emission tomography). A method for preparing [$^{18}$F]flumazenil by reacting a diaryliodonium salt precursor with the positron-emitting radionuclide fluorine-18. [$^{18}$F]flumazenil can be prepared from the diaryliodonium salt precursor in the presence of kryptofix$_{2.2.2}$/potassium carbonate($K_{2.2.2}/K_2CO_3$) and TEMPO in dimethylformamide (DMF) at a high yield.

3 Claims, 7 Drawing Sheets

FIG. 7 ized at a radiochemical yield of 10% or higher.

METHOD FOR PREPARATION OF FLUORINE-18-LABELED FLUMAZENIL USING DIARYLIODONIUM SALT PRECURSOR

CROSS-REFERENCE TO RELATED APPLICATIONS

This is a continuation application of International Application No. PCT/KR2011/004075 filed on Jun. 3, 2011, which claims priority to Korean Application No. 10-2011-0049726 filed on May 25, 2011, which applications are incorporated herein by reference.

TECHNICAL FIELD

The present invention relates to the preparation of [$^{18}$F]flumazenil. More particularly, the present invention relates to a method for synthesizing fluorine-18 [$^{18}$F]-labeled flumazenil ([$^{18}$F]flumazenil) from various diaryliodonium salts.

BACKGROUND ART

Most epilepsy patients show improved health with drug therapy, but no therapeutic influences are shown on about 10 to 15% of epilepsy patients. Thus, a surgical treatment of the brain lesion responsible for the onset of seizures is very important to drug therapy-resistant patients. In this regard, an epileptic lesion must be accurately detected, which is typically carried out by imaging and quantifying benzodiazepine receptors in epileptic lesion loci.

In a normal brain, high concentrations of benzodiazepine receptors are found at the cerebral cortex, the cerebellum, and the thalamus, with a low concentration detected at the caudate nucleus. Taking advantage of the fact that the concentration of benzodiazepine receptors is reduced in an epileptic lesion, the imaging of benzodiazepine receptors can be applied to the localization of the epileptic lesion and the diagnosis of epilepsy.

There are many diagnosis methods of an epileptic lesion including magnetic resonance imaging (MRI), single photon emission computed tomography (SPECT), positron emission tomography (PET), interictal electroencephalography, and ictal electroencephalography. Of them, MRI is the most widely used diagnosis method and can detect an epileptic lesion once the brain undergoes a syntactical change. In contrast, SPECT and PET can be applied to the detection of an epileptic lesion in the presence of even a biochemical change prior to the syntactical change, and thus have an advantage over MRI in terms of accurate diagnosis in the initial phase.

PET imaging of epileptic lesions can be understood based on the knowledge of the mechanism or biochemical change of epilepsy. The radiopharmaceutical fluorine-18-labeled fluoro-deoxyglucose ([$^{18}$F]FDG) is one of the most widely used for epilepsy imaging. Being involved in glucose metabolism in the brain, the radio-labeled fluoro-deoxyglucose can be used to visualize the metabolism activity of the brain, as evaluated for cerebral glucose metabolism by PET images. Extensive studies have been done on PET imaging of epileptic lesions with fluoro-deoxyglucose, reporting that epileptic regions exhibit a low level of glucose metabolism at the interictal phase. The brain, however, fundamentally exhibits a high fluoro-deoxyglucose uptake, so that the S/N (signal-to-noise) ratio is decreased. Further, the uptake influences the outskirt of the lesion, causing the false impression that a decreased level of the glucose metabolism might be detected over a scope wider than the practical lesion. In addition, because PET images of epileptic lesions using fluoro-deoxyglucose are poor in reliability, and are greatly affected by other compounds having influence on the glucose metabolism, or by physical conditions, the use of fluoro-deoxyglucose alone is limitedly applied to the diagnosis of epilepsy.

Among positron-emitting radionuclides used for PET, carbon-11 ($t_{1/2}$=20.4 min), nitrogen-13($t_{1/2}$=9.98 min), oxygen-15($t_{1/2}$=2.03 min), fluorine-18 ($t_{1/2}$=109.8 min), copper-64 ($t_{1/2}$=12.7 min), and iodine-124 ($t_{1/2}$=4.2 days) are produced in a cyclotron, and gallium-68 ($t_{1/2}$=68.03 min) in a generator. PET images obtained from carbon-1'-labeled flumazenil ([$^{11}$C]flumazenil), one of the most widely used benzodiazepine receptor antagonists, provide a more accurate localization for epileptic lesions than those from other radionuclides. [$^{11}$C]flumazenil is advantageous in that the benzodiazepine receptor-targeting pharmaceutical flumazenil does not undergo structural and chemical changes at all. However, the half life of 20 min of the radionuclide leaves no spare time for labeling operation and post-labeling processes. Further, [$^{11}$C]flumazenil emits a large dose of radiation and can be applied to up to 2 patients only, depending on the number of PET instruments.

On the other hand, the positron-emitting radionuclide fluorine-18 has a relatively long half life ($t_{1/2}$=109.8 min) and is easy to label to compounds through organic synthesis, so that it can be used in the synthesis of radiopharmaceuticals, which takes time, and the study of physiological metabolisms, which are typically slow progressing. Accordingly, preference is made for flumazenil labeled with fluorine-18 rather than fluorine-19 because it more effectively allows for the analysis of compounds for in vivo activity through real-time PET images. Thus far, the synthesis of [$^{18}$H]flumazenil ([$^{18}$F]FMZ) has been achieved by direct nucleophilic labeling of the nitromazenil (NO$_2$-mazenil) precursor, but with a radiochemical yield as low as 5 to 20%, so that the quantity obtained only satisfies the need for several persons' supply of radionuclide. In order to meet the demand of clinical research, an automatic synthesis apparatus has been applied, but resulted in a yield of 1% or lower. There has not yet been reports on the mass production of [$^{18}$F]flumazenil using an automatic synthesis apparatus. To overcome the problems encountered in the prior art, the flumazenil derivatives fluorine-18 fluoroethyl flumazenil ([$^{18}$F]FEFMZ, (5-(2'-[$^{18}$F]fluoroethyl)flumazenil)) and fluorine-18 fluoroflumazenil ([$^{18}$F]FFMZ, (2'-[$^{18}$F]fluoroflumazenil) have been developed, but they, different in chemical structure from flumazenil, exhibit different pharmacokinetic profiles. In addition, the fluorine-18 which is located on the aliphatic moiety is apt to undergo defluorination in vivo, resulting in low signal-to-noise ratios, and degrading the quality of flumazenil-based, benzodiazepine receptor PET images of the brain due to non-target images of fluorine-18-labeled metabolites. Hence, these radionuclides are not extensively applied to clinical research.

SUMMARY

In accordance with an aspect thereof, the present invention discloses a method for effectively preparing a radiopharmaceutical useful in PET for the diagnosis of an epileptic lesion, that is, a method for synthesizing [$^{18}$F]flumazenil at high yield, which is longer in half life than [$^{11}$C]flumazenil.

In this context, the present invention provides a diaryliodonium salt as a precursor from which [$^{18}$F]flumazenil, which has a longer half-life than, but the same pharmacokinetic profile as [$^{11}$C]flumazenil, can be synthesized at high yield, and this approach is extended to a viable method for use in automated synthesis with a high radiochemical yield.

Technical Solution

The present invention provides [$^{18}$F]flumazenil, which has a relatively long half life among the positron-emitting radionuclides for use in PET, and an optimal reaction condition for the synthesis of [$^{18}$F]flumazenil from the diaryliodonium salt precursors (8a to 8h).

Instead of the conventional nitro-mazenil (NO$_2$-mazenil) precursor, a diaryliodonium salt precursor is labeled with fluorine-18 in the present invention. Nucleophilic aromatic fluorination of a diaryliodonium salt precursor with fluorine-18 is based on the fact that fluorine-18 is selectively substituted on one aromatic ring moiety, which is smaller in electron density than the other moiety, with the iodine atom located between the two aromatic ring moieties. In consideration of the selective labeling of fluorine-18, eight diaryliodonium salt precursors which are different in electron density from one another are synthesized, and six of them are used for fluorine-18 labeling.

The labeling reaction is carried out in a solvent such as acetonirile (CH$_3$CN), N,N-dimethylformamide (DMF), and dimethyl sulfoxide (DMSO), and in the presence of a phase transition catalysis such as kryptofix$_{2.2.2}$/potassium carbonate (K$_{2.2.2}$/K$_2$CO$_3$) tetrabutylammonium hydroxide (TBAOH), and tetrabutylammonium bicarbonate (TBAHCO$_3$) in order to enhance the labeling reactivity of fluorine-18. Because the diaryliodonium salt precursors are unstable due to the radical production of their own in a heating or alkaline condition, they were monitored for labeling yield for various reaction times at various temperatures in the presence of the radical scavenger 2,2,6,6-tetramethylpiperidine-1-oxyl (TEMPO).

In the presence of the radical scavenger, a higher [$^{18}$F]flumazenil labeling yield was obtained in the reaction solvent dimethylformamide than in acetonitrile or dimethylsulfoxide. In addition, an optimal reaction temperature was observed at 150° C. When the phase transition catalyst is K$_{2.2.2}$/K$_2$CO$_3$, the best results were obtained from most of the precursors.

Of the six diaryliodonium salt precursors (8a to 8f), 2-thiophenyl-mazenil-iodonium tosylate (8b), 3-thiophenyl-mazenil-iodonium tosylate (8c), 4-methoxyphenyl-mazenil-iodonium tosylate (8d) and 3-methoxyphenyl-mazenil-iodonium tosylate (8e), which have relatively high electron densities, were expected to allow for high labeling yields. Contrary to what was expected, the highest labeling yield was obtained from 4-methylphenyl-mazenil-iodonium tosylate (8f) irrespective of base conditions, which indicates that electron densities of the two aryl groups of the diaryliodonium salt precursors, and the stability at labeling reaction under heating and base conditions play a key role in increasing aromatic fluorination with fluorine-18. That is, of the diaryliodonium salt precursors, 4-methylphenyl-mazenil-iodonium tosylate (8f) was evaluated to be the most suitable for the synthesis of [$^{18}$F]flumazenil because of its highest stability and reactivity under the conditions. In addition, the precursor was applicable to an automated apparatus for the mass production of 18-fluorine-labeled molecules.

Aromatic fluorination of diaryliodonium salt precursors with fluorine-18 in combination with purification through high performance liquid chromatography (HPLC) can be successfully applied to the synthesis of [$^{18}$F]flumazenil at a yield of 70~75% (up to 6-fold higher than conventional methods), and it took as short as 55 min in total to synthesize the fluorine-18-labeled molecules by the method. Accordingly, the present invention can synthesize [$^{18}$F]flumazenil within a short period of time at a high yield, making great contribution to the imaging study of benzodiazepine receptors, in spite of the radiation decay of the radioisotope with time.

In addition, the synthesis method of [$^{18}$F]flumazenil can be applied to an automated synthesis at a radiochemical yield of 69 to 71% (decay-corrected) with a radiochemical purity of >98% within a total period of about 60 min.

DETAILED DESCRIPTION

The terminology used in the specification and the appended claims should be construed as having meanings and concepts concordant to the spirit of the present invention in light of the principle under which the present inventors can define the concept of the terminology to elucidate the invention of their own in the best way.

In the synthesis method of [$^{18}$F]flumazenil according to one embodiment of the present invention, the diaryliodonium salt precursor is represented by the following Chemical Formula 1:

Chemical Formula 1 wherein Ar– is selected from the group consisting of the following aryl (Ar–) radicals: Aryl (Ar–) radicals and X⁻ is selected from among trifluoromethane sulfonate), perfluoro $C_2$-$C_{10}$ alkyl sulphonate, trifluoroacetate, tetraphenylborate), toluene sulfonate), Br⁻, and Cl⁻.

In the synthesis method of [¹⁸F]flumazenil according to another embodiment of the present invention, the diaryliodonium salt precursor is represented by the following Chemical Formula 2:

Chemical Formula 2

![Chemical Formula 2 structure]

wherein —Ar

![Ar structure with R¹, R², R³]

$R^1$~$R^3$ are independently selected from among H, $C_1$ alkyl, $C_2$ alkyl, $C_1$ haloalkyl, and $C_2$ haloalkyl, and X⁻ is selected from among trifluoromethane sulfonate, perfluoro $C_2$-$C_{10}$ alkyl sulphonate, trifluoroacetate, tetraphenylborate, toluene sulfonate, Br⁻, and Cl⁻.

Reference is now made to the following Reaction Scheme to delineate the synthesis of diaryliodonium tosylate precursors.

Isatoic anhydride (2) is heated in sarcosine and dimethyl sulfoxide to synthesize 4-methyl-1H-1,4-benzodiazepin-2,5-diaone (3). This 4-methyl-1H-1,4-benzodiazepin-2,5-diaone (3) is brominated with bromine in the presence of sodium acetate to give 7-bromo-4-methyl-1H-1,4-benzodiazepin-2,5-diaone (4). Then, 7-bromo-4-methyl-1H-1,4-benzodiazepin-2,5-diaone(4) is reacted with ethyl isocyanoacetate to afford imidazobenzodiazepine (ethyl 8-bromo-5,6-dihydro-5-methyl-6-oxo-4H-imidazo[1,5-a][1,4]benzodiazepine-3-carboxylate) (5). Ethyl 8-bromo-5,6-dihydro-5-methyl-6-oxo-4H-imidazo[1,5-a][1,4]benzodiazepine-3-carboxylate) (5) is substituted with tributyltin in the presence of tetrakis(triphenylphosphine)palladium [($Ph_3P)_4Pd$] to give an organic tine compound (ethyl 5,6-dihydro-5-methyl-6-oxo-8-tributylstannyl-4H-imidazo[1,5-a][1,4]benzodiazepine-3-carboxylate) (6). Then, the organic tine compound (ethyl 5,6-dihydro-5-methyl-6-oxo-8-tributylstannyl-4H-imidazo[1,5-a][1,4]benzodiazepine-3-carboxylate) (6) is reacted with hydroxy(tosyloxy)iodobenzene (Koser's reagent; [hydroxyl(tosyloxy)iodo]benzene) (7a) or various hydroxy(tosyloxy)iodoarenes (7b to 7h) to afford the diaryliodonium tosylate precursors (8a to 8h).

Reaction Scheme 1. Synthesis of diaryliodonium tosylate precursors

Figure 1:
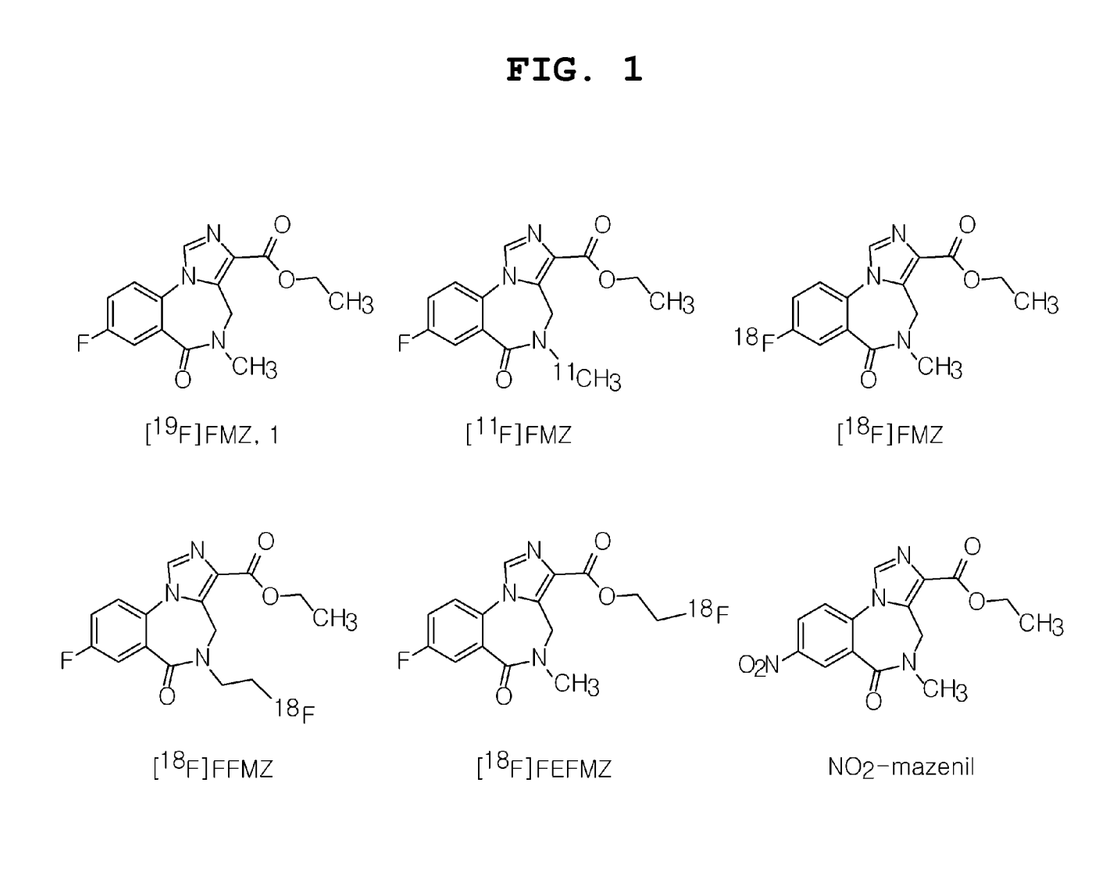
FIG. 1 shows structures of flumazenil derivatives with various radioisotopes introduced thereinto.
Figure 2:
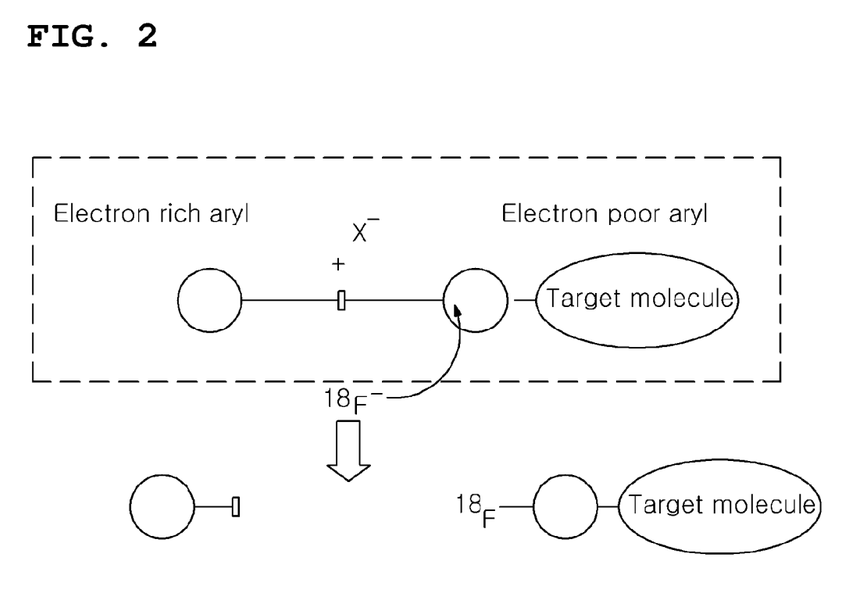
FIG. 2 is a schematic view illustrating a labeling reaction between a diaryliodonium salt and fluorine-18.

In order to label an aromatic ring with a nucleophile at a desired position, the aromatic ring generally must have an electron withdrawing group (EWG) at the ortho- or para-position. For example, the presence of a carbonyl or nitro group facilitates the substitution of fluorine-18 for a leaving group such as a nitro group or a halogen on an aromatic group. In contrast, the diaryliodonium salt can be advantageously labeled with the nucleophile fluorine-18 even in the absence of EWG. The labeling mechanism of fluorine-18 on a diaryliodium salt precursor is illustrated in FIG. 2 in which a fluorine-18 anion attacks an electron-poor aromatic moiety (B ring) rather than an electron-rich aromatic moiety. The richer the electron density of the B ring, the higher yield the aromatic fluorination of the A ring with fluoein-18.

Accordingly, various diaryliodonium salt precursors including phenyl-mazenil-iodonium tosylate (8a), 2-thiophenyl-mazenil-iodonium tosylate (8b), 3-thiophenyl-mazenil-iodonium tosylate (8c), p-methoxyphenyl-mazenil-iodonium tosylate (8d), m-methoxyphenyl-mazenil-iodonium tosylate (8e), p-methylphenyl-mazenil-iodonium tosylate (8f) m-methylphenyl-mazenil-iodonium tosylate (8g), and p-ethylphenyl-mazenil-iodonium tosylate (8h), all of which have rings richer in electron density, compared to mazenil, are prepared for use in labeling with fluorine-18.

Below, a description will be given of the reaction conditions under which [$^{18}$F]flumazenil is synthesized from the diaryliodonium tosylate precursors (8a to 8h).

Fluorine-18, produced in a cyclotron, was absorbed onto the cartridge of Chromafix® (PS-HCO$_3$), followed by elution with methanol/water containing a phase transition catalyst such as tetrabutylammonium bicarbonate, tetrabutylammonium hydroxide, or kryptofix$_{2.2.2}$/potassium carbonate (K$_{2.2.2}$/K$_2$CO$_3$). The resulting eluate was dried by azeotropic distillation, and the concentrate was stirred together with each of the diaryliodonium tosylate precursors (8a~8f) in 0.5 mL of a reaction solvent at a suitable temperature for 15 min. Labeling yields of fluorine-18 were monitored by silica gel-coated thin layer chromatography (TLC) developing with 10% methanol/dichloromethane, followed by detection with a radio-TLC (radio-thin layer chromatography) scanner.

For optimization of [$^{18}$F]flumazenil synthesis, labeling yields of [$^{18}$F]flumazenil were examined according to reaction temperatures, solvents, amounts and kinds of the diaryliodonium tosylate precursors, kinds of the phase transition catalyst, and molar ratios of the bases of the phase transition catalysts/precursors.

TABLE 1

Labeling Yield of Diaryliodonium Salt Precursors (8a to 8f) with [$^{18}$F] Flumazenil

| Entry[a] | Precursor | 100° C. | 125° C. | 150° C. |
|---|---|---|---|---|
| | | TBAHCO$_3$ | | |
| 1 | 8a | 6.3 | 20.7 | 24.6 (2.8[C]) |
| 2 | 8b | 1.2 | 4.1 | 6.3 |
| 3 | 8c | 1.8 | 4.0 | 3.4 |
| 4 | 8d | <1 | 1.3 (2.1[4]) | 2.5 |
| 5 | 8e | <1 | 1.2 | 2.3 |
| 6 | 8f | 15.4 | 23.1 | 21.1 |
| | | TBAOH | | |
| 7 | 8a | 8.2 | 11.0 | 13.2 |
| 8 | 8b | 3.6 | 5.7 | 10.1 |
| 9 | 8c | 4.5 | 7.1 | 7.7 |
| 10 | 8d | <1 | <1 | 2.3 |
| 11 | 8e | <1 | 1.4 | 2.7 |
| 12 | 8f | 11.7 | 15.6 | 17.7 |
| | | K$_{2.2.2}$/K$_2$CO$_3$ | | |
| 13 | 8a | 29.9 | 32.5 | 39.2 (6.4[d]) |
| 14 | 8b | 1.7 | 2.3 | 2.8 |
| 15 | 8c | 8.1 | 15.8 (11.7[e], 1.8[f]) | 6.8 |
| 16 | 8d | <1 | 1.1 | 1.5 |
| 17 | 8e | 1.4 | 1.3 | 1.3 |
| 18 | 8f | 20.7 | 55.1 (55.0[g]) | 74.1 (42.2h, 80.4i, 51.7j, 81.2k, 77.4l) |

[a]All reactions were carried out by stirring 8a to 8f (4 mg) together with various bases (0.8 eq.) in the presence of the 2,2,6,6-tetramethylpiperidine-1-oxyl (TEMPO) free radical scavenger (1 mg) at predetermined temperatures for 15 min in the dimethylformamide (DMF) solvent;
[b]Labeling yield of fluorine-18 determined by radio-TLC (n = 2 or 3);
[c]in the absence of 2,2,6,6-tetramethylpiperidine-1-oxyl radical scavenger (TEMPO);
[d]Reaction solvent: dimethylsulfoxide(DMSO);
[e]Reaction solvent: acetonitrile (CH$_3$CN);
[f]Reaction solvent: dimethylsulfoxide(DMSO);
[g]Reaction temp.: 135° C.;
hpotassium carbonate(K$_2$CO$_3$): 1.0 equivalent;
ipotassium carbonate(K$_2$CO$_3$): 0.6 equivalents;
jpotassium carbonate(K$_2$CO$_3$): 0.4 equivalents;
kpotassium carbonate(K$_2$CO$_3$): 0.6 equivalents and reaction time: 5 min;
lpotassium carbonate(K$_2$CO$_3$): 0.6 equivalents and 8f (8 mg), reaction time 15 min.

Table 1 summarizes data of [$^{18}$F]flumazenil prepared from diaryliodonium salt precursors (8a to 8f).

Among the various reaction conditions, the best result was obtained by reacting the precursors at 150° C. for 5 min in the presence of kryptofix$_{2.2.2}$/potassium carbonate (K$_{2.2.2}$/K$_2$CO$_3$) under 2,2,6,6-tetramethylpiperidine-1-oxyl (TEMPO) in N,N-dimethylformamide (DMF). 2,2,6,6-Tetramethylpiperidine-1-oxyl served as a radical scavenger to eliminate radicals produced as a by-product upon the fluorination of the diaryliodonium salt precursors with fluorine-18.

Since the diaryliodonium salt is unstable at high temperatures in an alkaline condition and split into aromatic hydrocarbons (H-mazenil) by radical degradation, a radical scavenger is employed. Reaction temperatures also have influences on the labeling yield of fluorine-18. At a temperature of 130° C. or higher, high labeling yields of fluorine-18 were obtained for most precursors and bases. In this experiment, it is recommended to conduct the reaction at lower than 160° C. for stable operation of an automated synthesis apparatus. Accordingly, the labeling reaction with fluorine-18 was monitored at 150° C.

In spite of the expectation that the mazenil aromatic ring of the diaryliodonium salt precursors (8b to 8e) might be labeled with fluorine-18 at high yields because of the contralateral aromatic moieties are richer in electron density than the mazenil moiety, their labeling yields with fluorine-18 were poor at high temperatures under an alkaline condition. From these low radiochemical yields, it is inferred that the stability shorter reaction time is preferred in consideration of the half life of the radioisotope, the reaction time was optimized to be 5 min.

Contrary to the expectation that the diaryliodonium salt precursors (8b to 8e) could be labeled at higher yields than precursor 8a thanks to their higher electron densities, a lower labeling yield of fluorine18 was detected for them at high temperatures in the presence of a base. This might be accounted by the significance of the stability of the precursors. To verify this, the precursors were analyzed for stability in the presence of fluorine-18. In addition, a reaction was carried out in the presence of base-free cesium fluoride (CsF) within a phase-transition catalyst to examine the reactivity of each precursor. In the following Reaction Scheme 2, the degradation of each diaryliodonium salt precursor in the presence of base under a heating condition is illustrated. As shown, two compounds I-mazenil (9) and H-mazenil (10) are formed, and their concentrations reflect the stability of the diaryliodonium salt precursor.

Reaction Scheme 2. Degradation of Diaryliodonium Tosylate Precursor

I-mazenil, 9

H-mazenil, 10 of the diaryliodonium salt precursors plays an important role in increasing the production of [$^{18}$F]flumazenil.

For most of the precursors, higher labeling yields of fluorine-18 were obtained in the presence of kryptofix$_{2.2.2}$/potassium carbonate (K$_{2.2.2}$/K$_2$CO$_3$) than tetrabutylammonium hydroxide and tetrabutylammonium bicarbonate. A molar ratio of 1/0.6 (80.4%) of the precursor to potassium carbonate gave a peak labeling yield, indicating that the molar ratio of the precursor to potassium carbonate is an important factor for the aromatic fluorination with fluorine-18.

Under the reaction conditions, given in Table 1, for labeling the diaryliodonium salts (8a to 8f) with fluorine-18, the amounts of the diaryliodonium tosylate precursor (8f) (4 mg vs 8 mg) had no significant influences on the yield. The labeling yield was not affected by the reaction time either, comparing 5 min (81.2%) with 15 min (80.4%). Because a The diaryliodonium salt precursors whose aromatic rings are richer in electron density, compared to phenyl-mazenil-iodonium salt (8a), are more apt to be affected by the reaction conditions for aromatic fluorination with fluorine-18. 4-Methylphenyl-mazenil-iodonium salt precursor (8f), although lower in electron density compared to 2-thiophenyl-mazenil iodonium salt, 3-thiophenyl-mazenil-iodonium salt, 3-methoxyphenyl-mazenil-iodonium salt, and 4-methoxyphenyl-mazenil-iodonium salt, was obtained at higher yields irrespective of alkaline conditions. This result indicates that the stability of the diaryliodonium salt precursors, together with their electron density, play an important role in aromatic fluorination with fluorine-18. In fact, compounds in the form of diaryliodonium salts are known to be unstable at a high temperature. To examine the selectivity and stability of the diaryliodonium salts, the production of the by-products I-mazenil (9) and H-mazenil(10) which are degraded from the precursors due to their instability in a condition free of fluorine-18 was analyzed using HPLC. The diaryliodonium tosylate precursors (8a to 8f) are degraded at high temperatures in the presence of a base into I-mazenil (9) through "A pathway" and H-mazenil(10) through "B pathway", as illustrated in Reaction Scheme 1.

Figure 6:
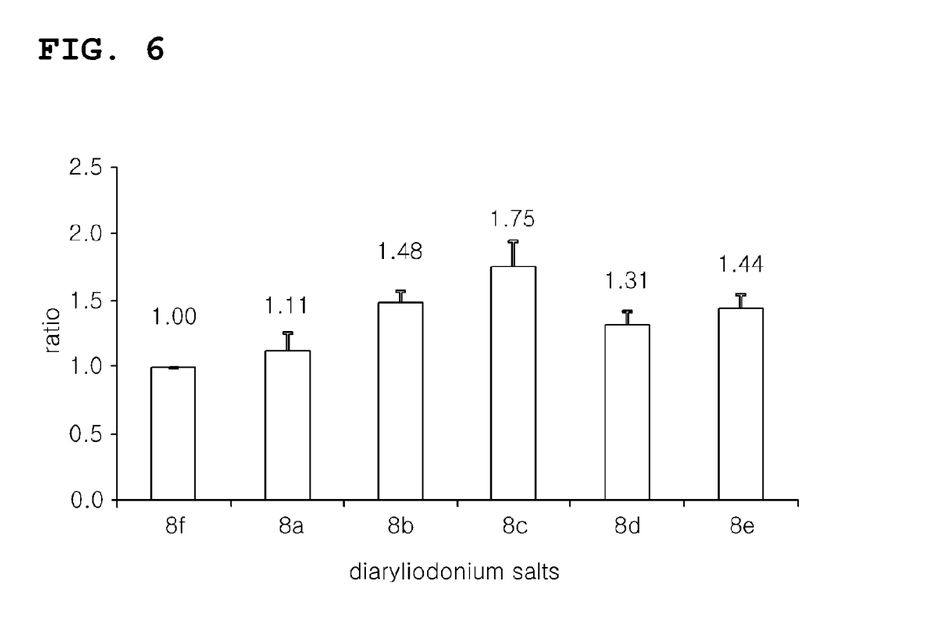
FIG. 6 is a graph showing relative instability of various diaryliodonium salt precursors under heating and base conditions of labeling.
Figure 7:
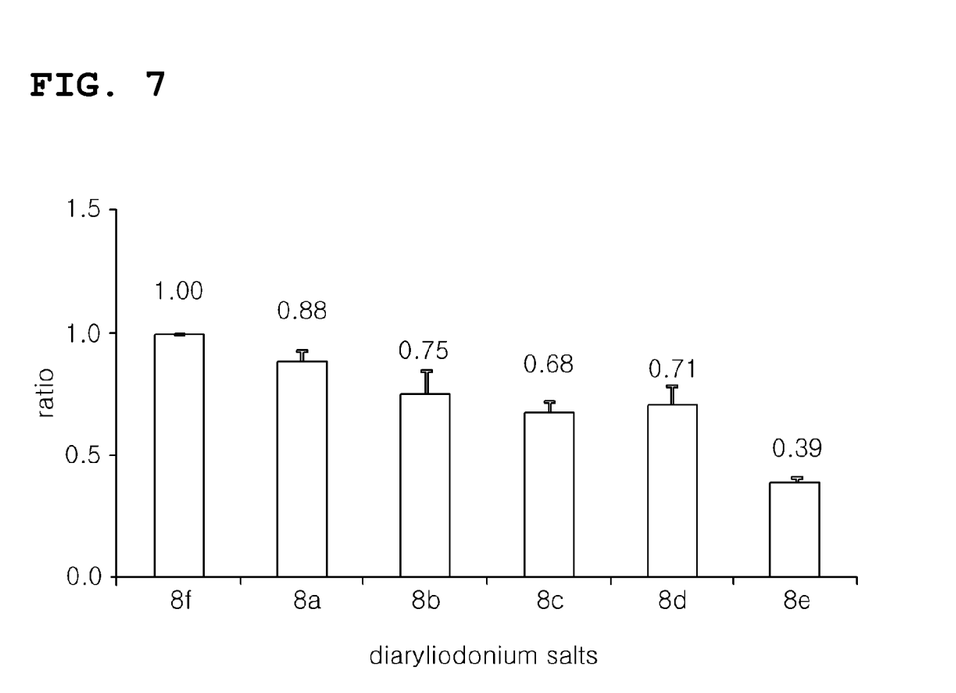
FIG. 7 is a graph showing relative reactivity of various diaryliodonium salt precursors in the presence of cesium fluoride (CsF).

After each diaryliodonium salt precursor was thermally treated 150° C. for 15 min in the presence of kryptofix$_{2.2.2}$/potassium carbonate ($K_{2.2.2}/K_2CO_3$) in dimethylformamide, without fluorine-18, measurement was made of the concentrations of 1-mazenil (9) and H-mazenil (10) to evaluate the stability of each precursor (FIG. 6). In addition, the labeling reactivity of the diaryliodonium salt precursors into [19F]flumazenil was assessed by reacting them with cesium fluoride at 90° C. for 120 min in dimethylformamide (FIG. 7). In FIG. 6, the stability of the precursors is shown. In the graph of FIG. 6, the y-axis is the ratio Among the diaryliodonium salt precursors, as can be seen in FIG. 6, the 4-methylphenyl-mazenil-iodonium salt (8f) is the most stable under the condition of potassium carbonate and 150° C., and similar results were obtained in the presence of other bases such as tetrabutylammonium bicarbonate and tetrabutylammonium hydroxide.

Assuming that the stability of 4-methylphenyl-mazenil-iodonium salt(8f) was set forth to be 1.00, the phenyl-mazenil-iodonium salt (8a) was similar in stability as indicated by 1.11, and the precursors (8b to 8e), although richer in electron density, were 1.31- to 1.75-fold more unstable than 4-methylphenyl-mazenil-iodonium salt (8f).

Results of the reactivity of the iodonium salts only under cesium fluoride are given in FIG. 7 where the Y-axis is represented by the ratio 4-methylphenyl-mazenil-iodonium salt (8f) was observed to be effectively fluorinated to [19F]flumazenil thanks to its thermal stability. Assuming that the reactivity of 4-methylphenyl-mazenil-iodonium salt (8f) (concentration of [F-18] FMZ) was set forth as 1.00, the reactivity of the other diaryliodonium salts (8a to 8e) was reduced to 0.39 to 0.88. Consequently, 4-methylphenyl-mazenil-iodonium salt (8f) is higher in both thermal stability and reactivity than the other diaryliodonium tosylates, which is why it can be fluorinated with fluorine-18 into [18F]flumazenil at the higher yield than can the other diaryliodonium tosylate precursors.

Figure 3:
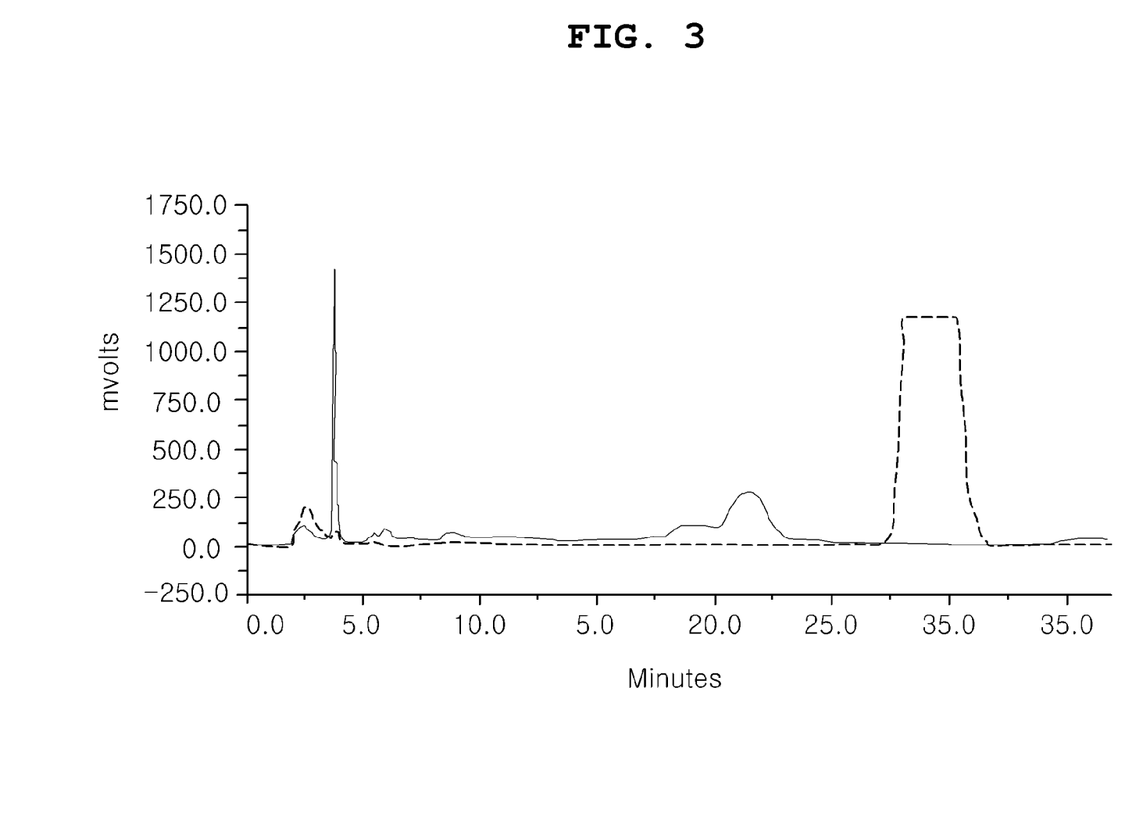
FIG. 3 is an HPLC chromatogram of [$^{18}$F]flumazenil [semi-preparative C-18 column; flow rate: 3 mL/min; solvent (20% CN$_3$CN:H$_2$O); black line: UV-254, red line: gamma ray].

Optimization of [$^{18}$F]flumazenil synthesis can be achieved by reacting 4 mg of 4-methylphenyl-mazenil-iodonium salt (8f) with fluorine-18 (about 3.7 GBq) at 150° C. for 5 min. in the presence of a phase transition catalyst (5.5 mg of kryptofix$_{2.2.2}$/potassium carbonate($K_{2.2.2}/K_2CO_3$)) and a radical scavenger in dimethylformamide. Under these conditions, [$^{18}$F]flumazenil was obtained at a radiochemical yield of 70 to 75%, which was up to 6-fold higher than conventional yields, with a radiochemical purity of 98% or higher after HPLC (FIG. 3). It took about 55 min in total to completely synthesize [$^{18}$F]flumazenil inclusive of the isolation and purification of the compound, with a specific activity of 140 to 244 GBq/mmol.

In addition, the optimum condition was applied to a commercially available automated synthesis apparatus, such as that identified as TracerLab FX-FN (GE Healthcare) to produce [$^{18}$F]flumazenil.

Figure 4:
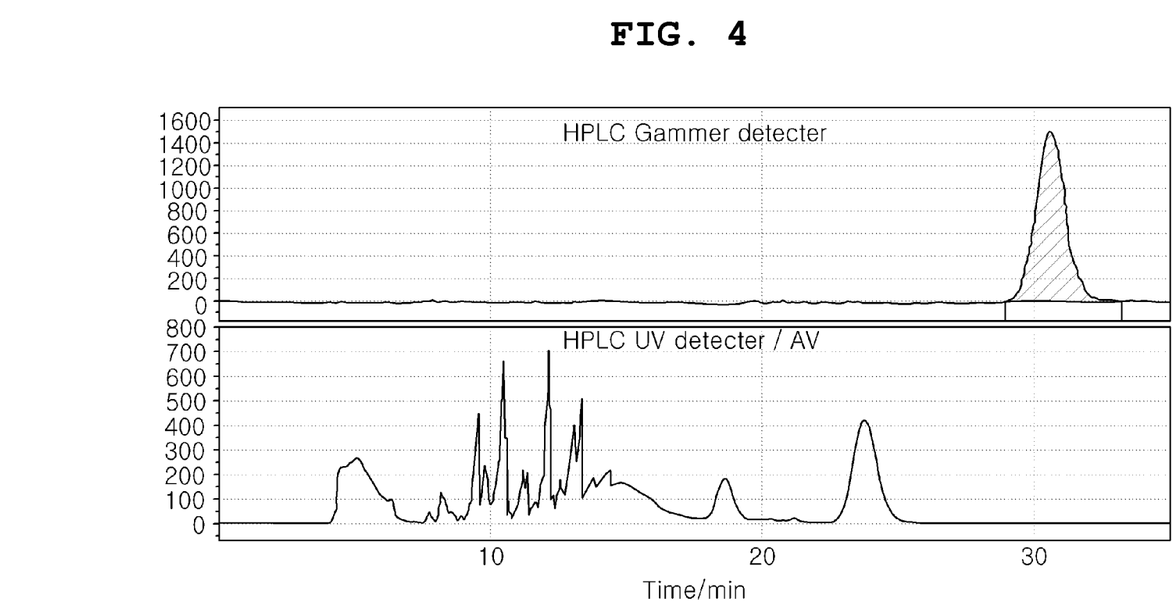
FIG. 4 is an HPLC chromatogram of [$^{18}$F]flumazenil in association with automated synthesis [semi-preparative C-18 column; flow rate: 4.5 mL/min; 용매 (20% CN$_3$CN:H$_2$O); gamma ray, bottom: upper: UV-254].

FIG. 4 shows an HPLC chromatogram of the products from the automated synthesis apparatus (TracerLab FX-FN). When each reagent vial was treated according to a conventional method for the production of a fluorine-18-labeled radiotracer, [$^{18}$F]flumazenil was synthesized in an automated way at a radiochemical yield of about 69 to 72% and a radiochemical purity of 98% or more, within a total time of about 60 min.

Figure 5:
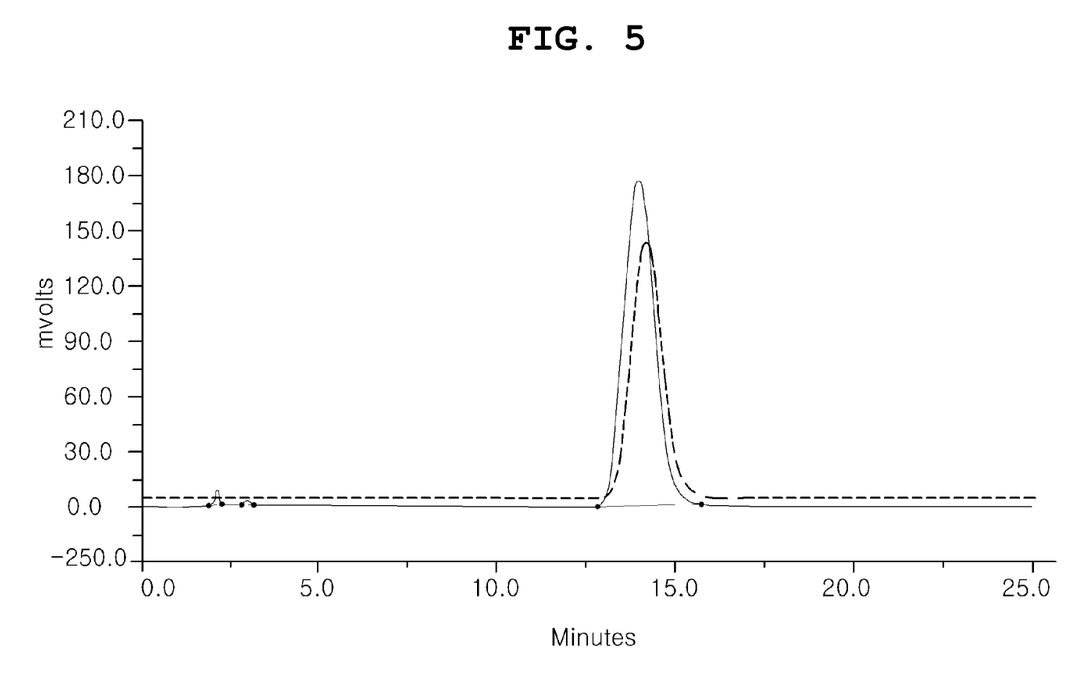
FIG. 5 is an HPLC chromatogram of [$^{18}$F]flumazenil and the standard substance [$^{19}$F]flumazenil (black line: UV-254, red line: gamma ray).

To examine whether [$^{18}$F]flumazenil was accurately synthesized in the automated synthesis apparatus, the [$^{18}$F]flumazenil purified by HPLC was loaded, together with the standard reference [$^{19}$F]flumazenil, to an HPLC column and eluted. Concurrent elution at the same time point (FIG. 5) proved the radiopharmaceutical synthesized under the conditions of the present invention to be [$^{18}$F]flumazenil.

A detailed description will be given with reference to the following Examples.

Unless stated otherwise, commercially available reagents and solvents were used without further purification. All reagents and solvents were purchased from Sigma-Aldrich (USA). Chromatography for the isolation of products from each reaction was conducted using silica gel (Merck, 230-400 mesh, ASTM), with all reactions monitored on a pre-coated plate (Merck, silica gel 60F$_{254}$). $^1$H- and $^{13}$C-NMR spectra were analyzed using Varian 400-MR (400 MHz) spectrometer, and expressed in parts per million (ppm, δ units). Water ($H_2^{18}O$) was purchased from Taiyo Nippon Sanso Corporation (Japan), and fluorine-18 was prepared through the $^{18}$O (p,n)F reaction by proton irradiation using KOTRON-13 cyclotron (Samyoung Unitech Co., Ltd.) in the Seoul National University Bundang Hospital. The Chromafix® PS-HCO$_3$ (45 mg) cartridge was obtained from Macherey-Nagel Ins. (Germany), and Sep-Pak®C18 plus cartridge was purchased from Waters Corp. (U.S.). HPLC was carried out using Gilson 322 equipped with an NaI radiodector (Raytest) and a UV-detector. HPLC-grade solvents (J. T. Baker, U.S.) were used after filtration through a membrane (0.22 μm, Whatman). Radio-TLC was monitored using a Bioscan radio-TLC scanner (Washington D.C., U.S.A.). All radiation doses were measured using a VDC-505 activity calibrator from Veenstra Instruments (Netherlands). Unless stated otherwise, the radiochemical purity was expressed after decay-correction. For automated synthesis, TracerLab FX-FN (GE Healthcare) was employed.

EXAMPLES

The synthesis of various diaryliodonium tosylate precursors (8a to 8h) is stepwise explained in detail, with isatoic anhydride (2) serving as a starting material.

Step 1: Preparation of
4-Methyl-1H-1,4-benzodiazepin-2,5-diaone (3)

A mixture of 6.09 g (37.3 mmol) of isatoic anhydride (2), 3.49 g (39.2 mmol) of sarcosine, and 40 mL of dimethylsulfoxide was heated to 180° C. for 2 hrs in a nitrogen atmosphere. The reaction mixture was cooled, diluted in water, and extracted three times with chloroform. The organic layer thus obtained was dried over anhydrous sodium sulfate, and concentrated. Recrystallization of the concentrate in methanol/dichloromethane afforded 5.58 g of 4-methyl-1H-1,4-benzodiazepin-2,5-diaone (3) as a white solid (79%) ($^1$H NMR (400 MHz, CDCl$_3$) δ 3.03 (s, 3H), 3.09 (s, 2H), 7.01 (d, J=7.6 Hz, 1H), 7.29 (t, J=7.6 Hz, 1H), 7.48 (td, J=7.6, 1.6 Hz, 1H), 7.97 (dd, J=8.0, 1.6 Hz, 1H), 8.63 (s, 1H)).

Step 2: Preparation of
7-Bromo-4-methyl-1H-1,4-benzodiazepin-2,5-diaone
(4)

To a solution of 1.53 g (8.04 mmol) of 4-methyl-1H-1,4-benzodiazepin-2,5-diaone(3) in 20 mL of acetic acid were slowly added 1.65 g (20.1 mmol) of sodium acetate and 1.03 g (20.1 mmol) of bromine (Br$_2$), followed by stirring the reaction mixture at room temperature for 24 hrs. Then, the reaction mixture was poured to 200 mL of ice water and filtered. Purification by flash column chromatography (5% methanol/dichloromethane) afforded 1.58 g of 7-bromo-4-methyl-1H-1,4-benzodiazepin-2,5-diaone (4) as a white solid (75%) ($^1$H NMR (400 MHz, CDCl$_3$) δ 3.29 (s, 3H), 3.90 (s, 2H), 6.91 (d, J=8.4 Hz, 1H), 7.57 (dd, J=8.4, 2.4 Hz, 1H), 8.09 (d, J=2.4 Hz, 1H), 8.77 (s, 1H)).

Step 3: Preparation of Ethyl 8-bromo-5,6-dihydro-5-methyl-6-oxo-4H-imidazo[1,5-a][1,4]benzodiazepine-3-carboxylate (5)

A solution of 5.00 g (18.6 mmol) of 7-bromo-4-methyl-1H-1,4-benzodiazepin-2,5-diaone (4) in 36 mL (1 mmol)/2 mL of dimethylformamide and 54 mL (1 mmol)/3 mL of tetrahydrofuran was cooled to 0° C., and dropwise added with 0.890 g (22.3 mmol) of 60% sodium hydride for 20 min with stirring. Thereafter, 4.80 g (27.9 mmol) of diethylphosphorochloridate was slowly added to the solution for 30 min in an ice bath while stirring. To the resulting reaction mixture, a solution of 2.52 g (22.3 mmol) of ethyl isocyanoacetate in 22 mL (1 mmol)/1 mL of dimethylformamide was dropwise added, together with 1.04 g (19.6 mmol) of a 60% sodium hydride solution, using a cannula. After the reaction was terminated with 1 mL of acetic acid, the reaction mixture was quenched with cold water and extracted with ethyl acetate. The organic layer thus obtained was washed with water and brine, and concentrated with anhydrous sodium sulfate to dryness. Purification by flash column chromatography (3% methanol/dichloromethane) afforded 2.00 g of ethyl 8-bromo-5,6-dihydro-5-methyl-6-oxo-4H-imidazo[1,5-a][1,4]benzodiazepine-3-carboxylate (5) as a white solid (29%) ($^1$H NMR (400 MHz, CDCl$_3$) δ 1.45 (t, J=7.2 Hz, 3H), 3.25 (s, 3H), 4.21-4.59 (m, 2H and 1H), 5.04-5.37 (m, 1H), 7.32 (d, J=8.4 Hz, 1H), 7.76 (dd, J=8.4, 2.4 Hz, 1H), 7.89 (s, 1H), 8.20 (d, J=2.4 Hz, 1H)).

Step 4: Preparation of Ethyl 5,6-dihydro-5-methyl-6-oxo-8-tributylstannyl-4H-imidazo[1,5-a][1,4]benzodiazepine-3-carboxylate (6)

To a solution of 3.52 g (9.67 mmol) of ethyl 8-bromo-5,6-dihydro-5-methyl-6-oxo-4H-imidazo[1,5-a][1,4]benzodiazepine-3-carboxylate (5) in 100 mL of toluene were dropwise added 16.8 g (29.0 mmol) of tributyltin and 0.335 g (0.290 mmol) of tetrakis (triphenylphosphine) palladium. The reaction mixture was heated under reflux in an Ar gas. The mixture was diluted in 100 mL of ethylacetate, and the organic layer thus formed was washed with water and concentrated. Purification by flash column chromatography (5% methanol/dichloromethane) afforded 3.72 g of ethyl 5,6-dihydro-5-methyl-6-oxo-8-tributylstannyl-4H-imidazo[1,5-a][1,4]benzodiazepine-3-carboxylate(6) as a white solid (66%). ($^1$H NMR (400 MHz, CDCl$_3$) δ 0.90 (t, J=7.2 Hz, 9H), 1.09-1.16 (m, 6H), 1.28-1.40 (m, 6H), 1.46 (t, J=7.2 Hz, 3H), 1.49-1.59 (m, 6H), 3.26 (s, 3H), 4.22-4.58 (m, 2H and 1H), 5.19 (d, J=14.8 Hz, 1H), 7.35 (d, J=8.0 Hz, 1H), 7.71 (dd, J=8.0, 1.2 Hz, 1H), 7.89 (s, 1H), 8.13 (d, J=0.8 Hz, 1H)).

Step 5: Preparation of Diaryliodonium tosylate
precursors (8a to 8h)

To a solution of each of the hydroxyl(tosyloxy)iodo-aryl moieties (7a to 7h) in 2 mL of acetonitrile, a solution of ethyl 5,6-dihydro-5-methyl-6-oxo-8-tributylstannyl-4H-imidazo[1,5-a][1,4]benzodiazepine-3-carboxylate (6) in 2 mL of dichloromethane (CH$_2$Cl$_2$) was dropwise added at room temperature under argon gas, followed by stirring for 20 hrs. After evaporation in a nitrogen atmosphere, the residue was dissolved in 1.0 mL of ethanol and transferred to a 20 mL vial. This solution was diluted with excess diethyl ether. It was centrifuged and the pellet was dried in a vacuum to afford the diaryliodonium tosylate precursors (8a to 8h).

Precursor 8a was ethyl 8-phenyl(iodonium tosylate)-5,6-dihydro-5-methyl-6-oxo-4H-imidazo[1,5-a][1,4]benzodiazepine-3-carboxylate ($^1$H NMR (400 MHz, CD$_3$OD) δ 1.41 (t, J=6.8 Hz, 3H), 2.34 (s, 3H), 3.21 (s, 3H), 4.30-4.51 (m, 2H and 1H), 5.13 (bs, 1H), 7.20 (d, J=8.0 Hz, 2H), 7.55 (td, J=7.8, 1.6 Hz, 2H), 7.66 (dd, J=6.8, 1.6 Hz, 2H), 7.71 (t, J=7.6 Hz, 1H), 7.81 (d, J=8.4 Hz, 1H), 8.27 (dd, J=8.4, 1.2 Hz, 2H), 8.30 (s, 1H), 8.48 (dd, J=8.8, 2.4 Hz, 1H), 8.72 (d, J=2.0 Hz, 1H)).

Precursor 8b was ethyl 8-(2-thiophenyl)(iodonium tosylate)-5,6-dihydro-5-methyl-6-oxo-4H-imidazo[1,5-a][1,4]benzodiazepine-3-carboxylate ($^1$H NMR (400 MHz, CD$_3$OD) δ 1.41 (t, J=7.0 Hz, 3H), 2.36 (s, 3H), 3.22 (s, 3H), 4.40-4.62 (m, 2H and 1H), 5.15 (bs, 1H), 7.20-7.23 (m, 3H), 7.69 (d, J=8.4 Hz, 2H), 7.84 (d, J=8.8 Hz, 1H), 7.94 (dd, J=5.2, 1.2 Hz, 1H), 8.10 (dd, J=3.6, 1.2 Hz, 1H), 8.31 (s. 1H), 8.47 (dd, J=8.8, 2.4 Hz, 1H), 8.73 (d, J=2.0 Hz, 1H)).

Precursor 8c was ethyl 8-(3-thiophenyl)(iodonium tosylate)-5,6-dihydro-5-methyl-6-oxo-4H-imidazo[1,5-a][1,4]benzodiazepine-3-carboxylate ($^1$H NMR (400 MHz, CD$_3$OD) δ 1.41 (t, J=7.2 Hz, 3H), 2.35 (s, 3H), 3.22 (s, 3H), 4.40-4.61 (m, 2H and 1H), 5.16 (bs, 1H), 7.20 (d, J=8.0 Hz, 2H), 7.67-7.71 (m, 3H), 7.73-7.75 (m, 1H), 7.82 (d, J=8.8 Hz, 1H), 8.30 (s, 1H), 8.44 (dd, J=8.4, 2.4 Hz, 1H), 8.60 (dd, J=2.8, 1.2 Hz, 1H), 8.70 (d, J=2.4 Hz, 1H)).

Precursor 8d was ethyl 8-(4-methoxyphenyl)(iodonium tosylate)-5,6-dihydro-5-methyl-6-oxo-4H-imidazo[1,5-a][1,4]benzodiazepine-3-carboxylate ($^1$H NMR (400 MHz, CD$_3$OD) δ 1.41 (t, J=7.2 Hz, 3H), 2.35 (s, 3H), 2.35 (s, 3H), 3.22 (s, 3H), 3.84 (s, 3H), 4.39-4.61 (m, 2H and 1H), 5.16 (bs, 1H), 7.08 (d, J=9.2 Hz, 2H), 7.21 (d, J=8.0 Hz, 2H), 7.68 (d, J=8.0 Hz, 2H), 7.81 (d, J=8.4 Hz, 1H), 8.17 (d, J=8.8 Hz, 2H), 8.30 (s, 1H), 8.41 (dd, J=8.8, 2.4 Hz, 1H), 8.66 (d, J=2.0 Hz, 1H)).

Precursor 8e was ethyl 8-(3-methoxyphenyl)(iodonium tosylate)-5,6-dihydro-5-methyl-6-oxo-4H-imidazo[1,5-a][1,4]benzodiazepine-3-carboxylate ($^1$H NMR (400 MHz, CD$_3$OD) δ 1.40 (t, J=7.2 Hz, 3H), 2.35 (s, 3H), 3.21 (s, 3H), 3.85 (s, 3H), 4.39-4.61 (m, 2H and 1H), 5.16 (bs, 1H), 7.23-7.26 (m, 3H), 7.46 (t, J=8.2 Hz, 1H), 7.68 (d, J=8.4 Hz, 2H), 7.78-7.88 (m, 3H), 8.29 (s, 1H), 8.46 (d, J=8.8, 2.0 Hz, 1H), 8.74 (d, J=2.0 Hz, 1H)).

Precursor 8f was ethyl 8-(4-methylphenyl)(iodonium tosylate)-5,6-dihydro-5-methyl-6-oxo-4H-imidazo[1,5-a][1,4]benzodiazepine-3-carboxylate (¹H NMR (400 MHz, CD₃OD) δ 1.41 (t, J=7.2 Hz, 3H), 2.35 (s, 3H), 2.41 (s, 3H), 3.22 (s, 3H), 4.39-4.61 (m, 2H and 1H), 5.16 (bs, 1H), 7.21 (d, J=8.4 Hz, 2H), 7.37 (d, J=8.4 Hz, 2H), 7.68 (d, J=8.0 Hz, 2H), 7.82 (d, J=8.4 Hz, 1H), 8.12 (d, J=8.4 Hz, 2H), 8.30 (s, 1H), 8.43 (dd, J=8.8, 2.4 Hz, 1H), 8.69 (d, J=2.4 Hz, 1H)).

Precursor 8g was ethyl 8-(3-methylphenyl)(iodonium tosylate)-5,6-dihydro-5-methyl-6-oxo-4H-imidazo[1,5-a][1,4]benzodiazepine-3-carboxylate (¹H NMR (400 MHz, CD₃OD) δ 1.40 (t, J=7.2 Hz, 3H), 2.35 (s, 3H), 2.37 (s, 3H), 3.21 (s, 3H), 4.35-4.57 (m, 2H and 1H), 5.11 (bs, 1H), 7.28-7.31 (m, 3H), 7.52 (t, J=8.0 Hz, 1H), 7.72 (d, J=8.4 Hz, 2H), 7.81-7.89 (m, 3H), 8.27 (s, 1H), 8.40 (d, J=8.4, 1.8 Hz, 1H), 8.84 (d, J=1.8 Hz, 1H)

Precursor 8h was ethyl 8-(4-ethylphenyl)(iodonium tosylate)-5,6-dihydro-5-methyl-6-oxo-4H-imidazo[1,5-a][1,4]benzodiazepine-3-carboxylate (¹H NMR (400 MHz, CD₃OD) δ 1.38 (t, J=6.8 Hz, 3H), 1.41 (t, J=7.2 Hz, 3H), 2.35 (s, 3H), 2.60 (q, 2H), 3.22 (s, 3H), 4.39-4.61 (m, 2H and 1H), 5.16 (bs, 1H), 7.22 (d, J=8.0 Hz, 2H), 7.36 (d, J=8.0 Hz, 2H), 7.70 (d, J=8.4 Hz, 2H), 7.84 (d, J=8.4 Hz, 1H), 8.11 (d, J=8.8 Hz, 2H), 8.28 (s, 1H), 8.35 (dd, J=8.8, 2.4 Hz, 1H), 8.76 (d, J=2.4 Hz, 1H))

Finally, the diaryliodonium tosylate precursors (8a-8f) obtained in step 5 were fluorinated to [¹⁸F]flumazenil, as follows.

Step 6: Preparation of Fluorine-18-Labeled Fluazenil ([¹⁸F]flumazenil)

After being produced using Cyclotron, fluorine-18 (3.7-37.0 GBq) was absorbed onto a Chromafix®(PS-HCO₃) cartridge and eluted with methanol/water containing a tetrabutylammonium bicarbonate, tetrabutylammonium hydroxide or kryptofix₂.₂.₂/potassium carbonate (K₂.₂.₂/K₂CO₃) base. The eluate was dried by azeotropic distillation with acetonitrile (0.5 mL×2), and the residue was mixed and reacted with the diaryliodonium tosylate precursor (8a to 8f) and TEMPO (1 mg) in 0.5 mL of a reaction solvent at a suitable temperature for 5 min or 15 min. The reaction mixture was cooled in an ice water and diluted with excess water before purification through C18 plus Sep-Pak. [¹⁸F]flumazenil was eluted from the Sep-Pak using acetonitrile, and purified by HPLC. The [¹⁸F]flumazenil fraction was diluted with excess water and isolated by C18 plus Sep-Pak. An ethanol fraction from the Sep-Pak was mixed with saline to prepare an up to 10% EtOH/saline solution harmless to the body.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:
1. A method for preparing fluorine-18-labeled flumazenil, comprising reacting a diaryliodonium salt precursor with fluorine-18 at 130 to 160° C. in the presence of a phase transition catalyst which is selected from the group consisting of kryptofix₂.₂.₂/potassium carbonate (K₂.₂.₂/K₂CO₃), tetrabutylammonium hydroxide (TBAOH), tetrabutylammonium bicarbonate (TBAHCO₃), cesium hydroxide (CsOH), and a combination thereof,
wherein the diaryliodonium salt precursor is represented by the following Chemical Formula 1:

Chemical Formula 1 wherein Ar– is selected from the group consisting of the following aryl (Ar–) radicals:

and X⁻ is selected from among trifluoromethane sulfonate), perfluoro C₂-C₁₀ alkyl sulphonate, trifluoroacetate, tetraphenylborate), toluene sulfonate), Br⁻, and Cl⁻.

2. The method of claim 1, wherein the reacting is carried out in the presence of 2,2,6,6-tetramethylpiperidine-1-oxyl (TEMPO) in a reaction solvent.

3. A method for preparing fluorine-18-labeled flumazenil, comprising reacting a diaryliodonium salt precursor with fluorine-18, wherein the diaryliodonium salt precursor is represented by the following Chemical Formula 2:

Chemical Formula 2 wherein —Ar is $R^1$~$R^3$ independently selected from among H, $C_1$ alkyl, $C_2$ alkyl, $C_1$ haloalkyl, and $C_2$ haloalkyl, and $X^-$ is selected from among trifluoromethane sulfonate, perfluoro $C_2$-$C_{10}$ alkyl sulphonate, trifluoroacetate, tetraphenylborate, toluene sulfonate, $Br^-$, and $Cl^-$.

* * * * *